United States Patent
Karasic et al.

(10) Patent No.: US 12,303,123 B2
(45) Date of Patent: May 20, 2025

(54) MENISCAL REPAIR DELIVERY DEVICE

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Geoffrey I. Karasic, Milton, MA (US); Matthew D. Cunningham, Lakeville, MA (US); Han Teik Yeoh, Hopkinton, MA (US); Rick Fu, Randolph, MA (US); Roger R. Cassidy, Pepperell, MA (US); Allison M. Stauffer, Brighton, MA (US); Belin Mirabile, Brookline, MA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 381 days.

(21) Appl. No.: 17/913,205

(22) PCT Filed: Apr. 5, 2021

(86) PCT No.: PCT/US2021/025715
§ 371 (c)(1),
(2) Date: Sep. 21, 2022

(87) PCT Pub. No.: WO2021/207048
PCT Pub. Date: Oct. 14, 2021

(65) Prior Publication Data
US 2023/0134233 A1    May 4, 2023

Related U.S. Application Data

(60) Provisional application No. 63/006,760, filed on Apr. 8, 2020.

(51) Int. Cl.
*A61B 17/04* (2006.01)
*A61B 17/00* (2006.01)
*A61B 17/06* (2006.01)

(52) U.S. Cl.
CPC .... *A61B 17/0401* (2013.01); *A61B 17/06166* (2013.01); *A61B 2017/00407* (2013.01);
(Continued)

(58) Field of Classification Search
CPC .... A61B 2017/0409; A61B 2017/0459; A61B 17/0401; A61B 2017/047;
(Continued)

(56) References Cited

U.S. PATENT DOCUMENTS 5,507,754 A * 4/1996 Green .............. A61B 17/06109
606/139
5,810,848 A * 9/1998 Hayhurst ............... A61B 17/04
606/232

(Continued)

OTHER PUBLICATIONS

JP Office Action dated Nov. 5, 2024 for JP Application No. 2022-554175, with translation, 6 pages.

*Primary Examiner* — Kelly J Bekker
*Assistant Examiner* — Zehra Jaffri
(74) *Attorney, Agent, or Firm* — ArentFox Schiff LLP; Joseph M. Maraia; Marlo Schepper Grolnic (57) ABSTRACT

Tissue repair devices include an advancement assembly comprising a rod portion configured to advance through a needle to expel first and second implants from the needle, a ratchet coupled to a proximal section of the rod portion and configured to advance the rod through the needle by axial and rotational movement, and an advancement member having a linear travel axis including a first bore connected to a second bore. A diameter of the first bore is smaller than a diameter of the second bore such that the first bore and the second bore comprise a stop. The rod portion has mechani- (Continued)

cal properties optimized to both conform to a needle curvature and provide sufficient compressive strength to expel implants from the devices.

17 Claims, 7 Drawing Sheets (52) U.S. Cl.
CPC ............... *A61B 2017/00831* (2013.01); *A61B 2017/0409* (2013.01); *A61B 2017/06052* (2013.01); *A61B 2017/0608* (2013.01)

(58) Field of Classification Search
CPC ......... A61B 2017/0469; A61B 17/8875–8894; A61B 17/7076–7082; A61F 2/0805
See application file for complete search history.

(56) References Cited

U.S. PATENT DOCUMENTS

| 2004/0153074 A1* | 8/2004 | Bojarski | A61B 17/0401 |
| | | | 606/232 |
| 2018/0116654 A1* | 5/2018 | Santangelo | A61B 17/0469 |

* cited by examiner

MENISCAL REPAIR DELIVERY DEVICE

CROSS-REFERENCE TO RELATED APPLICATIONS

This application is the U.S. national phase entry under 35 U.S.C. § 371 of International Application No. PCT/US2021/025715, filed Apr. 5, 2021, entitled MENISCAL REPAIR DELIVERY DEVICE the contents of which are incorporated herein by reference in their entirety for all purposes.

TECHNICAL FIELD

The present disclosure relates to devices and methods for repairing tissue.

BACKGROUND

Areas in the body where tissue can be surgically reattached to bone or can be surgically repaired when a tear forms in the tissue include, but are not limited to, the biceps tendon, the lateral collateral ligament in the knee, the medial collateral ligament in the knee, the meniscus in the knee, the popliteal ligament in the leg. Fibrous tissue wounds, such as muscle, ligament, and meniscal tears, can be repaired arthroscopically using sutures. Traditionally, to close a fibrous tissue wound, a surgeon would insert two suture needles into the tissue with sutures attached, thread the sutures across the wound, and then tie knots to fix the free ends of the sutures within the tissue.

To simplify the wound closure and to improve fixation, various types of devices, and tools for use in delivering the devices, have been developed. For example, some current meniscal repair devices utilize curved rigid needle tips to aid in reaching the appropriate regions of a damaged meniscus. Two implants, connected together using suture, are held by the needle. Once the desired meniscus repair location is reached, the needle is pushed through the meniscus and the first implant is deployed using a push delivery mechanism. The needle is then retracted from the meniscus, repositioned on the opposing side of the tear site, and pushed through the meniscus. The second implant is then deployed. The device is then removed, leaving a length of suture knotted in a manner to close the distance between the two implants when pulled. The knot is tightened by pulling on the length of suture and the suture is cut adjacent to the knot.

Typical repair devices employ a user manipulated push mechanism to move a first implant distally (push direction) out of the needle tip, followed by a passive retraction step to position the push mechanism behind a second implant, then move the second implant distally (push direction). These devices lack a means for user manipulated retraction (pull) of the push mechanism. For example, a number of all-inside technique meniscal repair devices use a push delivery mechanism that includes a push rod. The push rod is coupled to a user manipulated knob or trigger that moves the push rod distally to push out a first implant. Subsequently, the push rod must retract to a position proximal to the second implant so the implant can be subsequently pushed out when the knob or trigger is moved. The means of push rod retraction include compression springs, torsion springs, constant force springs, etc. When certain forces, such as the friction in the push mechanism, exceed the spring force, the push rod is unable to retract to a position suitable to deploy the second implant.

Furthermore, typical repair devices employ a rigid push rod that cannot easily conform to the curved needle tip geometry. The push rod is typically coupled to a user manipulated knob or trigger that moves the push rod distally to push out one or more implants. The push rod is typically fabricated from austenitic stainless steels, precipitation-hardening stainless steels, or nickel-titanium alloys, such as Nitinol. These materials exhibit the necessary compressive strength to withstand the compressive load needed to expel the implants. However, the mechanical properties for the common push rod materials are not optimized for compliance with needle curvature. Often, the needle curvature is altered during use by either bending the device manually prior to entering the joint space or by applying forces that flex the tip of the needle while in the joint space. The altered needle curvature can cause the push delivery mechanism to fail. Failure occurs by excessive force to push or the push rod portion of the push mechanism breaches the needle slot where the implants reside. Failure also occurs by failure of the push rod to retract so the second implant can be subsequently pushed out when the knob is advanced forward. The mechanical properties for common push rod materials have not been optimized to maintain low friction with added curvature, or a tortuous path.

Moreover, current techniques for pulling on the suture to close the distance between the two implants include wrapping the free suture end around the user's fingers, user's hand, or a surgical instrument, such as a pair of forceps. The suture is then pulled until a desired tension in the repair is achieved. Depending on the force required to tension the repair, tensioning the suture can be strenuous on the user and may even cause pain as the suture may constrict their fingers beyond comfort. Additionally, given the high lubricity of the material typically used in the construction of suture, the suture may slip during reduction when wrapped around a wet gloved finger.

SUMMARY

Described herein are tissue repair devices that provide a push-pull delivery mechanism that facilitates retraction of a push rod independent of spring force on the rod. The devices include a handle having a longitudinal axis and an elongated needle defining an axial bore extending from the handle, a first implant and a second implant connected by a suture and disposed at least partially within the axial bore of the needle, the second implant disposed proximal to the first implant, and an advancement assembly. The advancement assembly includes a rod portion configured to advance through the needle to expel the first and second implants, a ratchet coupled to a proximal section of the rod portion and configured to advance the rod through the needle by axial and rotational movement, and an advancement member having a linear travel axis including a first bore connected to a second bore. A diameter of the first bore is smaller than a diameter of the second bore such that the first bore and the second bore comprise a stop. The push-pull mechanism has mechanical properties optimized to both conform to needle curvature and provide sufficient compressive strength to expel implants from the devices. The disclosure also provides for a compliant push rod, or portion thereof, that allows for more reliable implant deployment via needles having various degrees of curvatures. Finally, the disclosure also provides for a suture having a bifurcated section which serves as a finger loop for ease of tensioning the suture.

In one aspect, the present disclosure relates to a tissue repair device. The device can include a handle having a longitudinal axis, and an elongated needle defining an axial bore extending from the handle. The needle can include a proximal end and a distal end. Further, the device includes a first implant and a second implant connected by a suture and disposed at least partially within the axial bore of the needle, the second implant disposed proximal to the first implant. In addition, the device can include an advancement assembly. The advancement assembly can include a rod portion configured to advance through the needle to expel the first and second implants from the distal end of the needle, and a ratchet coupled to a proximal section of the rod portion and configured to advance the rod through the needle by axial and rotational movement. The advancement assembly can include an advancement member, coupled to the ratchet member, having a linear travel axis including a first bore connected to a second bore. A diameter of the first bore is smaller than a diameter of the second bore such that the first bore and the second bore define a stop. Further, the advancement assembly can include a push-pull mechanism moving on the linear travel axis, including a mating rod. The first bore of the advancement member can receive a section of the mating rod. The mating rod can have a stop member including a barb on its distal end. In a first position, the push-pull mechanism engages the stop and, in a second position, the push-pull mechanism is proximal to the stop.

In some embodiments, the rod includes Nitinol. In some embodiments, the Nitinol is Martensitic phase Nitinol. In some embodiments, a tensile strain of the Nitinol is about 50 ksi.

In some embodiments, the advancement assembly includes a plunger to permit a user to engage the push-pull mechanism in order to advance the first implant and the second implant from the distal end of the needle.

In some embodiments, the distal end of the needle includes a slot. In some embodiments, at least one of the first implant and the second implant includes a main body having a cross-section approximating the axial bore of the needle and a protrusion mating with the slot to preclude rotation of the implant in the needle.

In some embodiments, the device further includes a depth tube limiting the depth that the needle may be inserted into a tissue. In some embodiments, the depth tube has a depth tube lock for locking a linear position of the depth tube. In some embodiments, the depth tube includes a tapered distal portion.

In some embodiments, the device further includes a needle housing coupled to the handle. In some embodiments, the depth tube lock is operatively coupled to the needle housing.

In some embodiments, the distal end of needle has curved geometry. In some embodiments, a curve of the curved geometry is in-line with a slot of the distal end of the needle. In some embodiments, a curve of the curved geometry is away from the slot of the distal end of the needle.

In some embodiments, the device further includes one or more stops configured to limit the advancement of the ratchet member at predefined increments.

In some embodiments, the ratchet member is configured to return to a final position proximally aligned with a starting position of the ratchet member after expelling at least one of the first and second implants.

In some embodiments, the suture includes a sliding knot.

In some embodiments, an internal surface of the advancement member includes a plurality of teeth configured to engage the ratchet member.

In some embodiments, the ratchet member includes two radially extending tabs configured to alternately engage and disengage with a plurality of channels positioned within the advancement member.

In some embodiments, the barb includes a lead-in portion configured to facilitate a press fit into the first bore of the advancement member.

In another aspect, the present disclosure relates to a method of tissue repair. The method can include inserting a first anchor into tissue, the tissue including a tear, the first anchor being inserted into the tissue on a first side of the tear. The method can also include inserting a second anchor on a second side of the tear, the second anchor coupled to the first anchor via a knotted flexible member having a finger-engageable bifurcated portion. The method can also include, using the bifurcated portion, pulling on the flexible member to reduce a length of the flexible member between the first and second anchors, closing the first and second sides of the tear. In some embodiments, a size of the bifurcated portion is fixed.

BRIEF DESCRIPTION OF THE DRAWINGS

Various aspects of at least one embodiment of the present disclosure are discussed below with reference to the accompanying figures. It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. For purposes of clarity, not every component may be labeled in every drawing. The figures are provided for the purposes of illustration and explanation and are not intended as a definition of the limits of the invention.

DETAILED DESCRIPTION

In the following detailed description, numerous specific details are set forth in order to provide a thorough understanding of the embodiments of the present disclosure. It will be understood by those of ordinary skill in the art that these embodiments may be practiced without some of these specific details. In other instances, well-known methods, procedures, components and structures may not have been described in detail so as not to obscure the described embodiments.

Prior to describing at least one embodiment in detail, it is to be understood that the claims are not limited in their application to the details of construction and the arrangement of the components set forth in the following description or illustrated in the drawings. Also, it is to be understood that the phraseology and terminology employed herein are for the purpose of description only and should not be regarded as limiting.

Figure 1A:
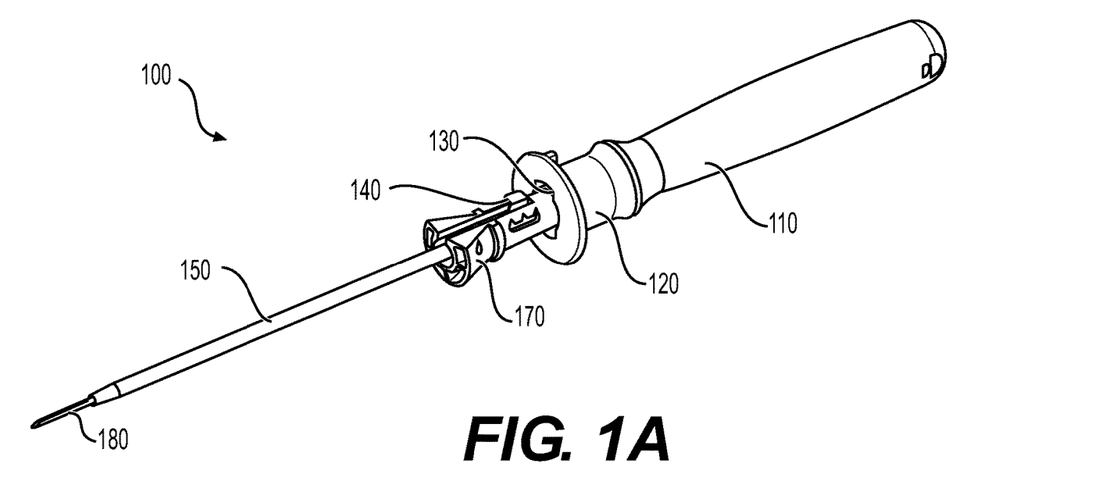
FIGS. 1a and 1b illustrate an system for tissue repair, according to certain embodiments.
Figure 1B:
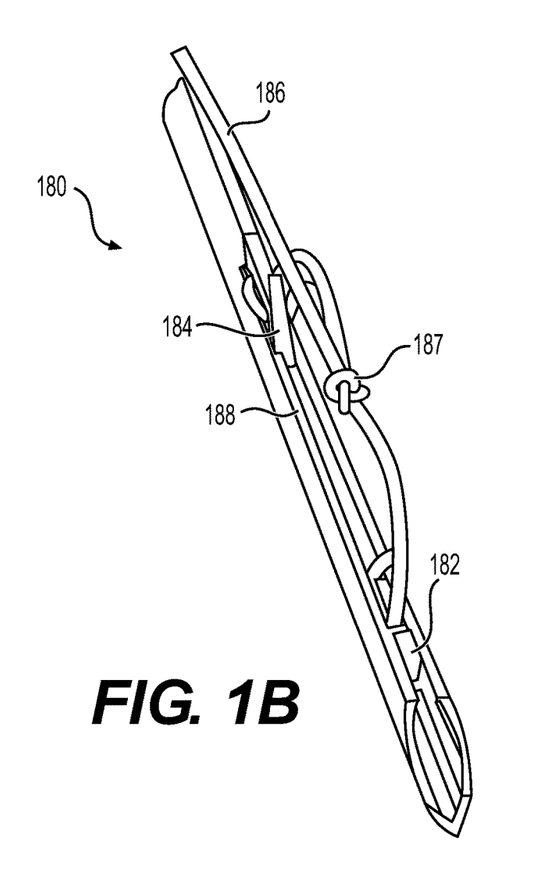

FIG. 1a illustrates an example of a tissue repair device 100 of this disclosure in an assembled view. The device 100 generally includes a handle 110, a knobbed plunger 120 coupled to the handle 110, a stationary housing 130 disposed within the knobbed plunger 120 and the handle 110, and a needle housing 170 coupled to the stationary housing 130. A depth tube lock 140 is disposed within the needle housing 170 and coupled to a depth tube 150. A needle 180 extends through the depth tube 150 and houses a first implant 182 and a second implant 184 connected by a suture 186 within an axial bore 188 (FIG. 1b) for deployment from the needle 180 into tissue. The suture 186 includes a sliding knot 187 to facilitate in reducing a length of the suture 186 between the implants 182, 184. The two implants 182, 184 reside in the distal portion of the needle 180 prior to deployment. The depth tube may include a tapered distal portion to facilitate easy entry into entry portals of tissue. The depth tube 150 and the depth tube lock 140 provide a means to limit the penetration of the needle 180. The interface between the knobbed plunger 120 and the handle 110 is a slip fit as is the fit between the implants 182, 184 and the needle 180. In use, the user would typically hold the device 100 by the handle 110 or the needle housing 170 positioned on either side of the knobbed plunger 120. The user pushes the knobbed plunger 120 forward to deploy the first implant 182 from the distal tip of the needle 180. After repositioning the needle on the opposing side of a tear, a second user manipulation of the knobbed plunger 120 is needed to deploy the second implant 184. The suture 186 is then pulled or otherwise tensioned to reduce a length of the suture 186 between the implants 182, 184, closing the tear. Other non-limiting examples of the handle 110, the knobbed plunger 120, the stationary housing 130, the depth tube lock 140, the depth tube 150, the needle housing 170, the needle 180 and the implants 182, 184 are disclosed in U.S. Pat. No. 8,888,798 and U.S. Publication No. 2018/0116654 to Smith & Nephew, Inc., the entire contents of which are incorporated herein by reference.

Figure 2A:
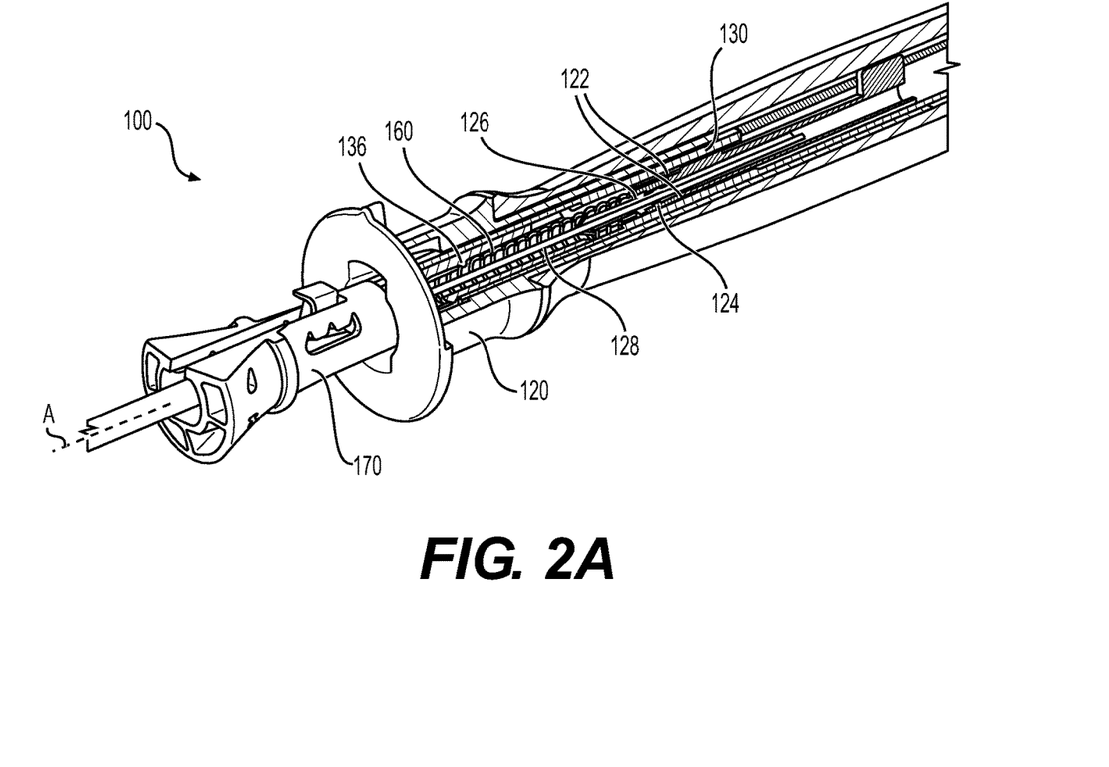
FIGS. 2a and 2b illustrate a ratchet mechanism of the tissue repair system, according to certain embodiments.

FIG. 2a illustrates a portion of the tissue repair device 100 of FIG. 1 in a cross-sectional view. As shown in FIG. 2a, an internal surface of the knobbed plunger 120 includes a plurality of teeth 122. The teeth 122 are configured to successively engage a ratchet member 124 which is rotatably and axially coupled to a push mechanism 126 to successively deploy the implants 182, 184. A cylindrical rod portion 128 of the push mechanism 126 is contained within the needle 180. A compressed spring 160 provides a linear force intended to maintain contact between the ratchet member 124 and the teeth 122 of the knobbed plunger 120. The spring 160 also provides a retraction force for the push mechanism 126 after implant deployment. The spring 160 further facilitates rotation of the ratchet member 124 relative to the teeth 122 of the knobbed plunger 120. The engagement of the ratchet member 124 with each successive tooth 122, along with engagement between the sidewalls of the tabs 125 of the ratchet member 124 and the channel walls of the stationary housing 130, provides a tactile and audible indication of a deployment of the corresponding first implant 182 or second implant 184.

Figure 2B:
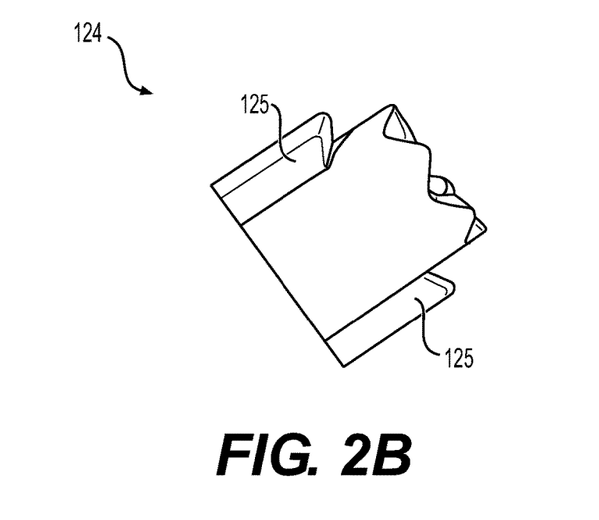

As shown in FIG. 2b, the ratchet member 124 contains two radially extending tabs 125 that, during forward deployment, alternately engage and disengage with several channels positioned radially within the wall of the stationary housing 130. The tabs 125 of the ratchet member 124 slide within internal channels along the axis of the stationary housing 130, providing radial alignment prior to deployment of each implant 182, 184. The push mechanism 126 moves distally along a travel axis A when the user retracts the knobbed plunger 120. The distal tip of the push mechanism 126 is protracted linearly until the tabs 125 of the ratchet member 124 contact a first discrete stop member 136 of the stationary housing 130, resulting in deployment of the first implant 182. The discrete stops are in radial alignment with the inner channels of the stationary housing 130 to prevent the push mechanism 126 from advancing during deployment of the implants 182, 184.

Figure 3:
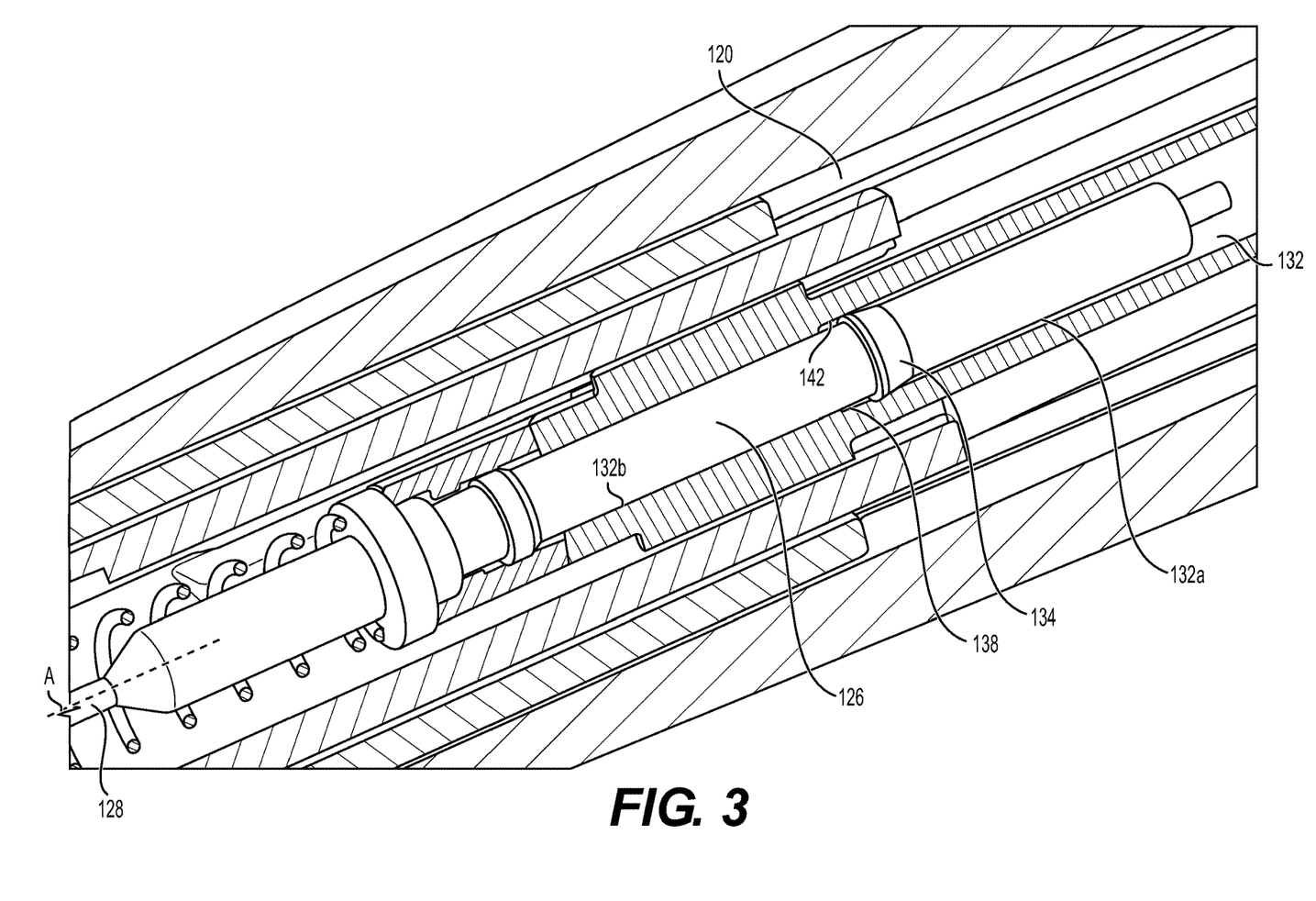
FIGS. 3 and 4 illustrate a push-pull mechanism of the tissue repair system, according to certain embodiments.

As shown in FIG. 3, the push mechanism 126 shares a common linear travel axis A with the knobbed plunger 120. The knobbed plunger 120 has an inner bore 132 configured to receive the rod portion 128 of the push mechanism 126. The inner bore 132 of the knobbed plunger 120, in conjunction with the distal bore of the needle 180 (FIG. 1), maintain alignment of the push mechanism 126. The push mechanism 126 also includes a stop feature, such as an annular barb 134. The inner bore 132 of the knobbed plunger 120 includes a proximal first portion 132a having an inner diameter selected to be larger than a distal second portion 132b, creating a counter bore 138 between the first portion 132a and the second portion 132b. The outer diameter of the barb 134 is selected to be larger than the second portion 132b of the inner bore 132, but less than the outer diameter of first portion 132a. When assembled, the linear position of the barb 134 is proximal to the linear position of the counter bore 138 in the knobbed plunger 120, such that a gap 142 exists between the barb 134 and the counter bore 138.

Figure 4:
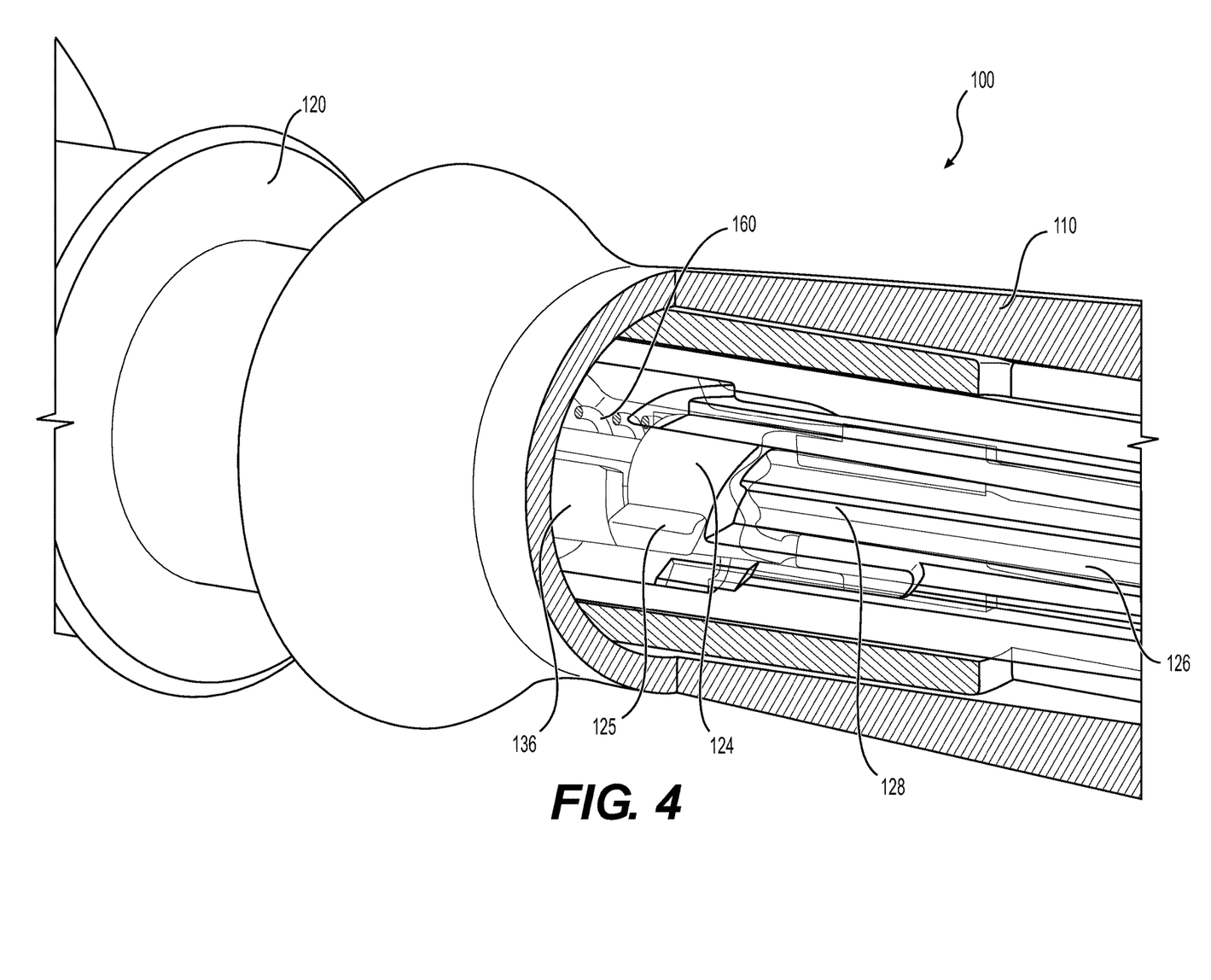

FIG. 4 shows the device 100 after the knobbed plunger 120 has been pushed distally until the tabs 125 of the ratchet member 124 contact a first discrete stop member 136, causing deployment of the first implant 182. The spring 160 creates a retraction force sufficient to retract the push mechanism 126 slightly. The small amount of retraction allows the ratchet member 124 to rotate and position the push mechanism 126 at an interim rest position. However, when the combined friction and bending forces between the rod portion 128 of the push mechanism 126 and the inner bore 188 of the needle 180 exceeds the spring force, the push mechanism 126 will not retract. This prevents the radial alignment of the ratchet member 124 to occur, preventing the push mechanism 126 from advancing distally to deploy the second implant 184.

Figure 5A:
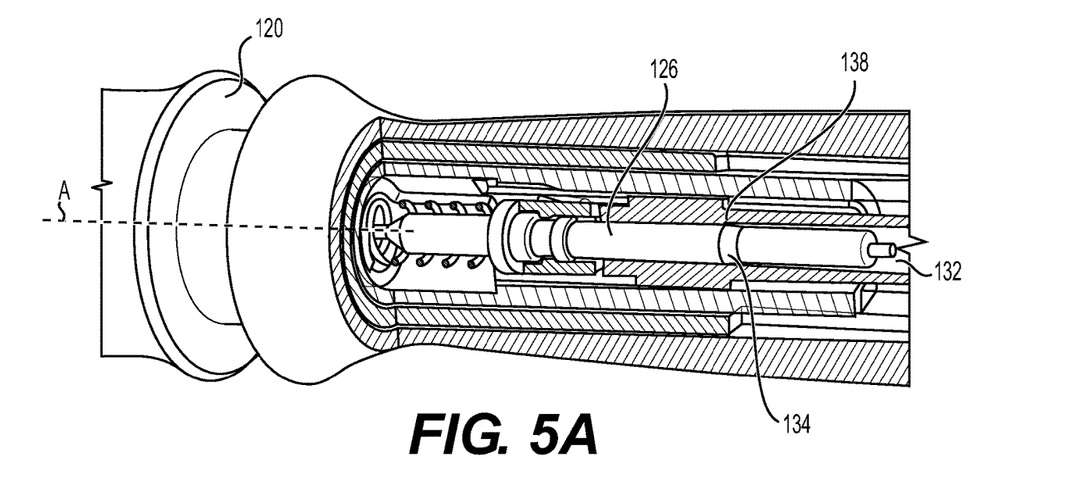
FIGS. 5a-c further illustrate the push-pull mechanism of the tissue repair system, according to certain embodiments.
Figure 5B:
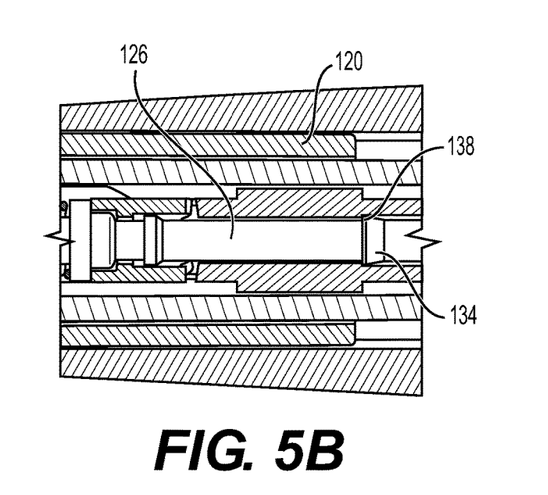
Figure 5C:
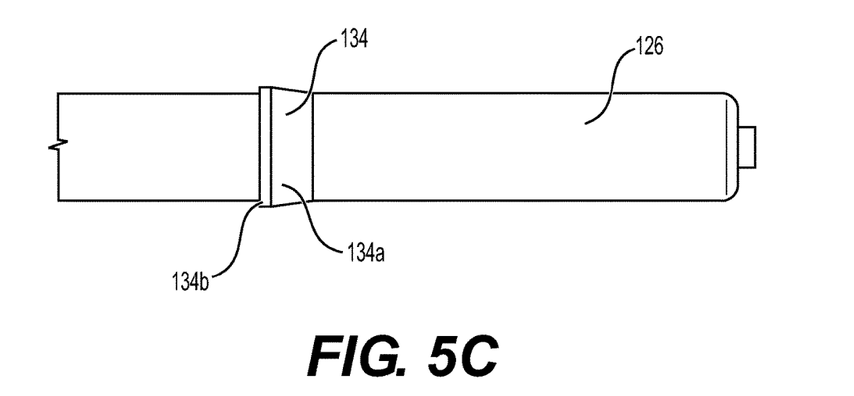

FIGS. 5A and 5B show the relative positions of the push mechanism 126 and the knobbed plunger 120 when the user retracts the knobbed plunger 120. As shown, retraction of the knobbed plunger 120 causes contact between the mating axial walls of the barb 134 in the push mechanism 126 with the annular counter bore 138 of the knobbed plunger 120. Thus, the push mechanism 126 will retract with the knobbed plunger 120, restoring device functionality that is compromised from use-related errors. As shown in FIG. 5C, the barb 134 of the push mechanism 126 includes a lead-in portion 134a to facilitate a press fit into the inner bore 132 of the knobbed plunger 120. An annular feature 134b on the barb 134 provides sufficient structural strength to oppose the forces impeding proximal axial motion of the push mechanism 126. The amount of diametric interference is sufficient to oppose the axial force impeding proximal axial motion, but not so high as to impede assembly of the two components. During retraction, the normal operating gap 142 between the barb 134 of the push mechanism 126 and the counter bore 138 is reduced until the mating faces contact. Once contact is made, the push mechanism 126 moves proximally along the travel axis A when the user advances the knobbed plunger 120. The push mechanism 126 will retract with the knobbed plunger 120 until the knobbed plunger 120 reaches the proximal stop position. Thus, the delivery device of the present disclosure provides an alternative means to retract the push mechanism 126 and allow the ratchet member 124 to rotate to a radial position suitable for deployment of the second implant 184 when the spring force alone is insufficient to retract the push mechanism 126.

In some embodiments, not shown, the annular coupling feature could be created in the knobbed plunger 120 with a corresponding undercut in the push mechanism 126. A multi-component coupling feature could also provide equivalent functionality. For example, a retaining ring could be pressed onto the push mechanism 126 after assembly into the bore 132 of the knobbed plunger 120.

Figure 6A:
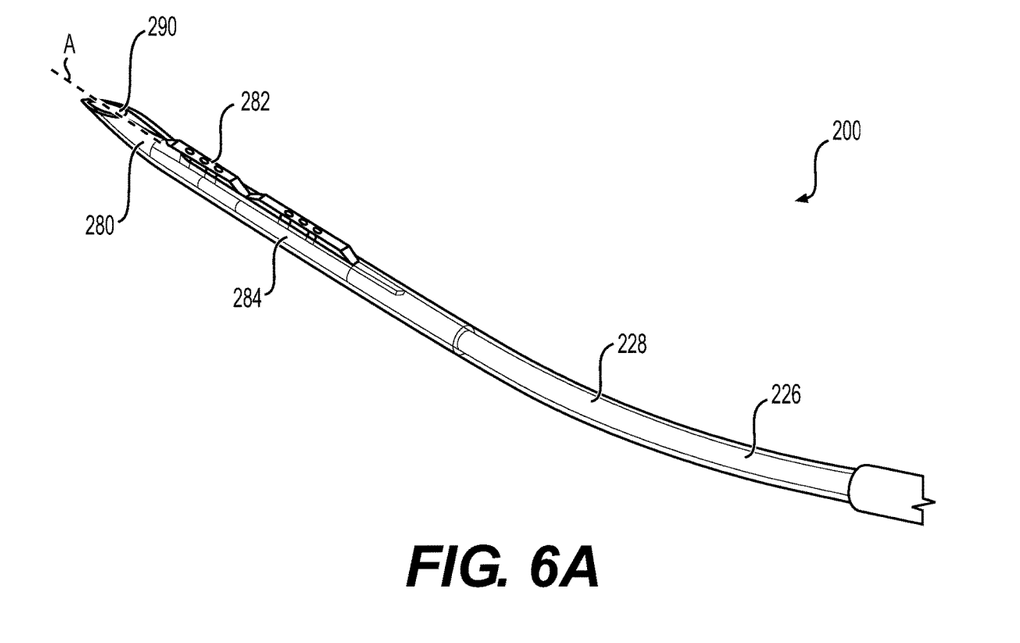
FIGS. 6a and 6b illustrate another system for tissue repair, according to certain embodiments.

As shown in FIG. 6A, another example of a tissue repair device 200 of this disclosure includes a needle 280 and a push mechanism 226 that share a common linear travel axis A. Two implants 282, 284 reside in the distal end of the needle 280. FIG. 6A also shows a needle 280 with significant curvature. In examples, the curvature of the needle 280 is in-line with the slot 290 in the distal portion of the needle 280. The push mechanism 226 includes a rod portion 228 configured to advance through the needle 280 to expel the first and second implants 282, 284 from the distal end of the needle 280. In examples, the rod portion 228 is comprised of operating-temperature, martensitic phase Nitinol. Martensitic phase Nitinol advantageously exhibits a lower elastic modulus than an austenitic material. For a given diameter of the rod portion 228, the martensitic rod maintains a residual strain at a lower push force than an austenitic rod having the same cross-sectional area and shape. When the material is mechanically loaded at a temperature below the Martensite finish temperature (Mf), or completely martensitic, the material remains strained when subsequently unloaded. The original shape can be recovered upon heating above the austenite finish temperature (Af). In examples, the stress of the Nitinol measured at 3% strain during tensile loading is about 50 ksi.

Figure 6B:
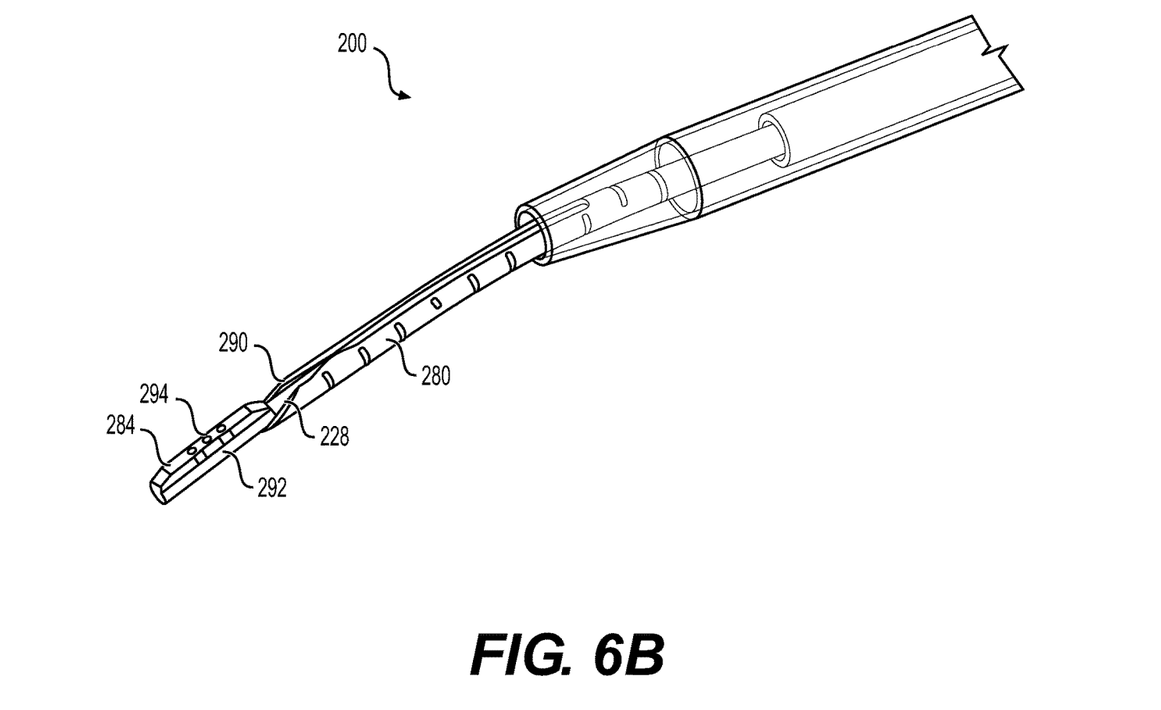

FIG. 6b depicts the device 200 having needle curvature in a direction opposing the slot 290 (reverse curvature). This direction of curvature is a challenge, since the distal tip of the rod portion 228 is not supported while being advanced distally. Common push rod materials exhibit sufficient mechanical stiffness to deform the slot 290 and breach the needle bore 288. When breach occurs, the push rod 228 will not expel the implant 284. The rod portion 228 of this disclosure conforms to the reverse needle curvature by having optimized mechanical properties and deforming at a force lower than the force required to breach the bore 288 of the needle 280 in the region of the slot 290. Proper function is maintained during distal advancement of the push mechanism 226 to expel the implants from the distal end of the needle 280. In examples, at least one of the first implant 282 and the second implant 284 comprises a main body 292 having a cross-section approximating the axial bore 288 of the needle 280 and a protrusion 294 mating with the slot 290 to preclude rotation of the implant 282, 284 in the needle 280.

In some embodiments, the push rod 228 could be fabricated having one or more portions having a lower flexural modulus, achieved by heat treating a portion of the push rod 228 to achieve the desired flexural strength. A multi-segment push rod 228 could comprise a distal tip portion having a first diameter and a proximal rod portion having a second diameter, said second diameter less than the first diameter. A multi-component push rod 228 could have the tip portion constructed from a different material, to decrease friction. The push rod 228 could include a distal tip portion having material removed (cuts) to increase flexibility.

Figure 7:
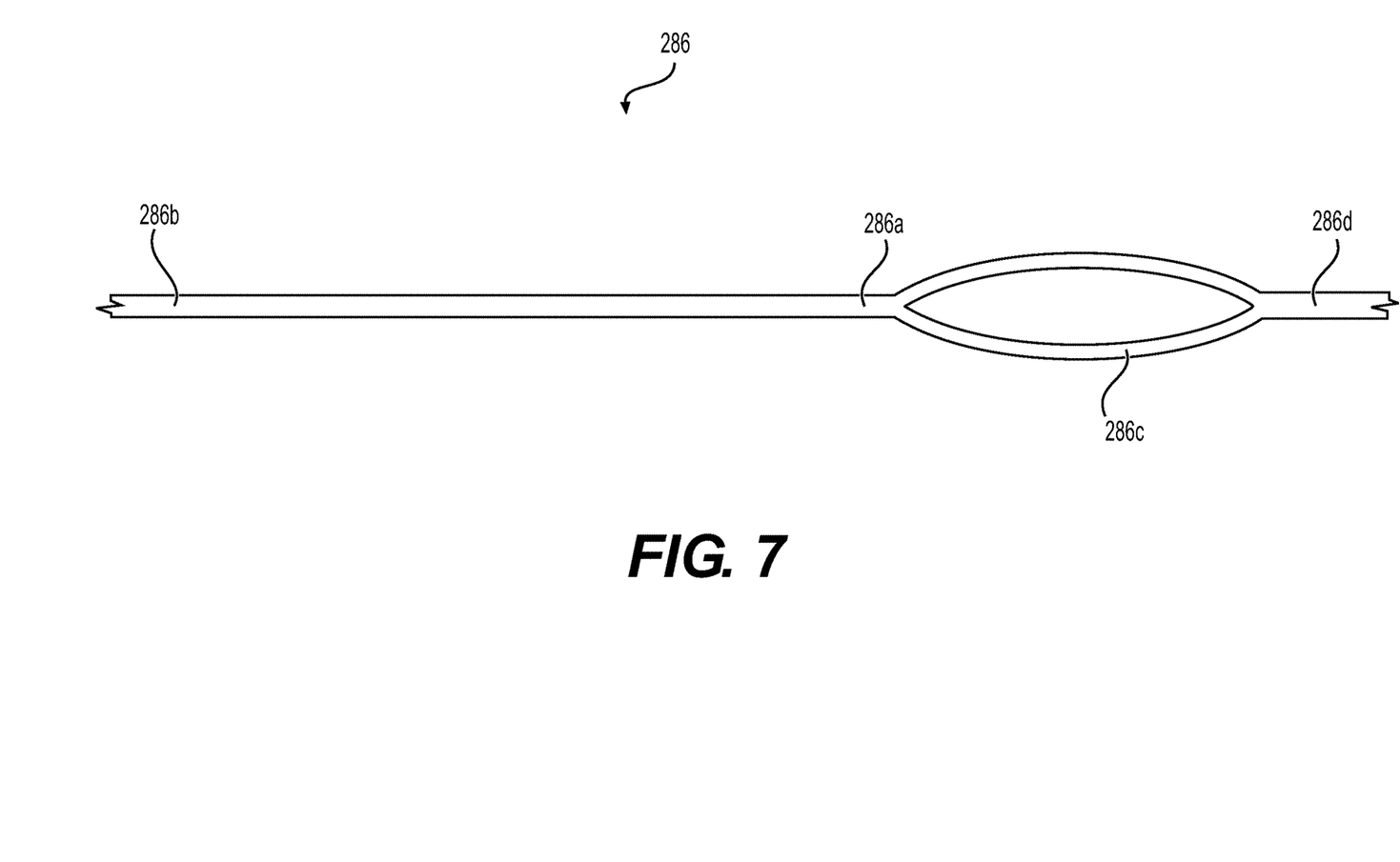
FIG. 7 illustrates a suture for use with the system for tissue repair, according to certain embodiments.

FIG. 7 shows a suture 286 having a proximal end 286a and a distal end 286b. The distal end 386b is configured for being coupled to implants of a tissue repair device, such as the tissue repair devices 100, 200 described above. The proximal end 286a is configured to exit a joint space and includes has a bifurcated section 286c and a tail 286d. The bifurcated section 286c serves as a loop, allowing the user to pass a number of fingers through. In the bifurcated section 286c, half of the fiber strands used to create the suture 286 form each segment of the loop, effectively creating a divergence and convergence of the suture 286. The bifurcated section 286c is large enough to fit multiple fingers so that the user can pull the suture 286 to the desired repair tension. This bifurcated section 286c is of a fixed diameter and will not cause any user discomfort when under tension. In examples, stiffening techniques ensure that the bifurcated section 286c remains open even when wet and is easily visible to the user. These stiffening techniques may include heat-stiffening or "shape-setting" of the suture 286 by heating the suture 286 to its glass-transition temperature and allowing it to cool around a mandrel of a specific shape and size. Other examples of stiffening techniques include providing a monofilament core in each segment of the bifurcated section 286c. In other examples, not shown, the suture 286 may include a full loop instead of a bifurcated section 286c to maintain the same diameter along the entire length of the suture 286, and not include a tail 286d. It is further contemplated that suture 286 could contain multiple bifurcated sections 286c of the same or different sizes along the length of the suture 286.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Whereas many alterations and modifications of the disclosure will no doubt become apparent to a person of ordinary skill in the art after having read the foregoing description, it is to be understood that the particular embodiments shown and described by way of illustration are in no way intended to be considered limiting. Further, the subject matter has been described with reference to particular embodiments, but variations within the spirit and scope of the disclosure will occur to those skilled in the art. It is noted that the foregoing examples have been provided merely for the purpose of explanation and are in no way to be construed as limiting of the present disclosure.

Although the present disclosure has been described herein with reference to particular embodiments, the present disclosure is not intended to be limited to the particulars disclosed herein; rather, the present disclosure extends to all functionally equivalent structures, methods and uses, such as are within the scope of the claims.

The invention claimed is:

1. A tissue repair device comprising:
a handle having a longitudinal axis;
an elongated needle defining an axial bore extending from the handle, the needle including a proximal end and a distal end;
a first implant and a second implant connected by a suture and disposed at least partially within the axial bore of the needle, the second implant disposed proximal to the first implant; and
an advancement assembly comprising:

a rod portion configured to advance through the needle to expel the first and second implants from the distal end of the needle;

a ratchet member coupled to a proximal section of the rod portion and configured to advance the rod portion through the needle by axial and rotational movement;

an advancement member, coupled to the ratchet member, having a linear travel axis including a first bore connected to a second bore, a diameter of the first bore is smaller than a diameter of the second bore such that the first bore and the second bore define a stop; and a push-pull mechanism moving on the linear travel axis, including a mating rod;

wherein the first bore of the advancement member receives a section of the mating rod, the mating rod having a stop member including a barb on its distal end, wherein in a first position, the push-pull mechanism engages the stop and, in a second position, the push-pull mechanism is proximal to the stop.

2. The tissue repair device of claim 1, wherein the rod portion comprises Nitinol.

3. The tissue repair device of claim 2, wherein the Nitinol is Martensitic phase Nitinol.

4. The tissue repair device of claim 3, wherein a tensile strain of the Nitinol is about 50 ksi.

5. The tissue repair device of claim 1, wherein the advancement assembly comprises a plunger to permit a user to engage the push-pull mechanism in order to advance the first implant and the second implant from the distal end of the needle.

6. The tissue repair device of claim 1, wherein:

the distal end of the needle includes a slot; and at least one of the first implant and the second implant comprises a main body having a cross-section approximating the axial bore of the needle and a protrusion mating with the slot to preclude rotation of the respective at least one of the first implant and the second implant in the needle.

7. The tissue repair device of claim 1, further comprising a depth tube limiting the depth that the needle may be inserted into a tissue.

8. The tissue repair device of claim 7, wherein the depth tube comprises a depth tube lock for locking a linear position of the depth tube.

9. The tissue repair device of claim 8, further comprising a needle housing coupled to the handle, and wherein the depth tube lock is operatively coupled to the needle housing.

10. The tissue repair device of claim 1, wherein the distal end of the needle has curved geometry.

11. The tissue repair device of claim 10, wherein a curve of the curved geometry is in-line with a slot of the distal end of the needle.

12. The tissue repair device of claim 10, wherein a curve of the curved geometry is away from a slot of the distal end of the needle.

13. The tissue repair device of claim 1, further comprising one or more stops configured to limit the advancement of the ratchet member at predefined increments.

14. The tissue repair device of claim 1, wherein the suture comprises a sliding knot.

15. The tissue repair device of claim 1, wherein an internal surface of the advancement member comprises a plurality of teeth configured to engage the ratchet member.

16. The tissue repair device of claim 1, wherein the ratchet member includes two radially extending tabs configured to alternately engage and disengage with a plurality of channels positioned within the advancement member.

17. The tissue repair device of claim 1, wherein the barb comprises a lead-in portion configured to facilitate a press fit into the first bore of the advancement member.

* * * * *